United States Patent
Kogan

(10) Patent No.: US 6,704,390 B2
(45) Date of Patent: Mar. 9, 2004

(54) X-RAY ANALYSIS APPARATUS PROVIDED WITH A MULTILAYER MIRROR AND AN EXIT COLLIMATOR

(76) Inventor: Vladimir Kogan, Lelyweg 1, 7602 EA Almelo (NL)

( * ) Notice: Subject to any disclaimer, the term of this patent is extended or adjusted under 35 U.S.C. 154(b) by 138 days.

(21) Appl. No.: 09/862,287

(22) Filed: May 22, 2001

(65) Prior Publication Data

US 2002/0003859 A1 Jan. 10, 2002

(30) Foreign Application Priority Data

May 29, 2000 (EP) .............................................. 00201887

(51) Int. Cl.[7] ................................................ G21K 1/06
(52) U.S. Cl. ........................................ 378/84; 378/147
(58) Field of Search ........................ 378/84, 147, 150, 378/82, 85, 49

(56) References Cited

U.S. PATENT DOCUMENTS

| 5,914,997 A | * | 6/1999 | Van Egeraat | ................ | 378/45 |
| 6,226,349 B1 | * | 5/2001 | Schuster et al. | .............. | 378/84 |

OTHER PUBLICATIONS

Mai, "Modern x–ray mirrors for perfect parallel beams", Materials World, Oct. 1999, pp. 616–618.*
"Modern X–Ray Mirrors for Perfect Parallel Beams", Materials World, Oct. 1999, pp. 616–618.

* cited by examiner

*Primary Examiner*—Craig E. Church
*Assistant Examiner*—Chih-Cheng Glen Kao
(74) *Attorney, Agent, or Firm*—Jensen & Puntigam P.S.

(57) ABSTRACT

The parallel radiation (12) emanating from a sample 4 in a known apparatus for X-ray analysis (for example, for diffraction) is analyzed according to wavelength and focused in a focus 20 by a parabolic multilayer mirror 14. A collimator 28 is positioned around said focus. The resolution of the apparatus can be enhanced by making the angular passage width of the collimator smaller than the maximum range of its reflection angle $\alpha_{max}$. In accordance with the invention the resolution of the apparatus will be better defined and hence enhanced by implementing the exit collimator 28 in such a way that the angular value for the passage width from every reflecting point A or B of the mirror surface is substantially independent of the position of the reflecting points. Preferably, the exit collimator 28 is implemented in the form of two mutually parallel knife edges which are situated at different distances from the reflecting points of the multilayer mirror.

5 Claims, 2 Drawing Sheets

X-RAY ANALYSIS APPARATUS PROVIDED WITH A MULTILAYER MIRROR AND AN EXIT COLLIMATOR

FIELD OF THE INVENTION

The invention relates to an apparatus for X-ray analysis of a sample, including
- an X-ray source for irradiating the sample by means of X-rays,
- an X-ray detector for detecting X-rays emanating from the sample,
- a parabolic multilayer mirror which is arranged in the beam path between the sample and the detector and has an associated reflection angle range $\alpha_{max}$, and
- a first collimator that is arranged at the area of the focus of the parabolic multilayer mirror.

BACKGROUND OF THE INVENTION

In apparatus for X-ray analysis, such as apparatus for X-ray fluorescence or for X-ray diffraction, a sample is irradiated by X-rays originating from an X-ray source which is generally a conventional X-ray tube. Sometimes it is important to parallel the radiation incident on the sample as well as possible, that is, to ensure that the various directions of the radiation within the X-ray beam enclose only a small angle relative to one another. The measurements are thus rendered practically unsusceptible to shape deviations of the sample (for example, in the case of X-ray powder diffraction the sample surface facing the incident beam need not be flat to a very high degree), to location-dependency in the X-ray absorption by the sample, and to locational deviations of the sample as a whole. Moreover, the angle of incidence of the X-rays is then suitably defined; this is of importance notably for X-ray diffraction with a high resolution.

From the article "Modern X-ray mirrors for perfect parallel beams" published in "Materials World", October 1999, pp. 616–618, it is known to make the X-rays originating from an X-ray source parallel and monochromatic by means of a parabolic multilayer mirror and to irradiate the sample to be analyzed by means of such a parallel monochromatic beam. The radiation originating from the sample is incident on another parabolic multilayer mirror which reflects the radiation in the direction of a collimator slit that is arranged in front of the X-ray detector and also ensures that undesirable wavelengths are removed from the reflected beam. Said collimator slit is provided at the area of the focus of said other parabolic multilayer mirror.

SUMMARY OF THE INVENTION

It is an object of the invention to realize a resolution which is better than that obtained by means of the arrangement that is known from the cited article. To this end, the X-ray analysis apparatus according to the invention is characterized in that the first collimator is arranged in such a manner that it exhibits substantially the same angular value of the angular passage width from every reflecting point of the multilayer mirror, and that said angular value, viewed from every reflecting point of the multilayer mirror, is smaller than the maximum reflection angle range $\alpha_{max}$.

The invention is based on the following insight. A multilayer mirror for X-rays has only a limited range of the reflection angle; this range is represented by the reference $\alpha_{max}$. In practical multilayer mirrors this range may have a value of the order of magnitude of 0.05°. When the parabolic multilayer mirror has a focal distance F, this means that an incident quasi-parallel beam with an angular spread $\alpha_{max}$ is imaged in the vicinity of the focus of the parabola with a width $F*\alpha_{max}$. If the passage width of the collimator is greater than this width of the image, such a passage width will have no effect on the resolution of the apparatus.

The passage width, however, does have an effect on the removal of background radiation: the X-rays incident on the first collimator consist of desired radiation emanating from the sample and of undesired radiation. The desired radiation is the radiation emanating from the sample at a desired angle. All other radiation (the background radiation), originating from the sample at an undesired angle as well as from the environment, must be stopped as much as possible by the first collimator.

When the passage width is chosen to be smaller than the width of said image, a part of the radiation present in the image is blocked. This can be done, for example, by means of a customary collimator that is formed by two flat knife edges arranged in one and the same plane. The knife edges are situated at a given distance from one another, thus creating a slit-like passage opening having a given slit width. Radiation that is incident on the multilayer mirror with an angular spread corresponding to said width could thus be blocked so that an angular range can be selected that is even smaller than said $\alpha_{max}$, thus enhancing the angular resolution of the apparatus.

The latter possibility however, would be limited if every reflecting point of the multilayer mirror were to produce a different magnitude of said image. In that case the resolution will no longer be suitably defined and, moreover, will be determined to an important degree by the point situated furthest from the focus. This is because for such a point the magnitude of the image is proportional to the distance between the relevant reflecting region and the location of the image. Because the first collimator is arranged in such a manner that it has approximately the same angular value for the passage width from any reflecting point of the multilayer mirror, every reflecting point thus makes the same contribution to the resolution of the apparatus.

In a preferred embodiment of the invention the angular value for the passage width of the first collimator that is observed from the reflecting mirror surface is adjustable. This embodiment offers not only the advantage that all regions of the entire multilayer mirror offer the same resolution, but also that the properties of the apparatus can be adapted to the measuring circumstances; alternatively, the collimator can be adapted to different multilayer mirrors that can be arranged in the apparatus.

In a further advantageous embodiment of the invention the first collimator is formed by two mutually parallel knife edges which are situated at different distances from the reflecting points of the multilayer mirror. This embodiment can be simply manufactured and, if desired, can also be readily constructed so as to be adjustable.

In a further embodiment of the invention the knife edges of the collimator are displaceable relative to one another by displacement transversely of the direction of the beam path through the collimator. The passage width of the collimator, and hence the resolution of the apparatus, is thus controlled without introducing deviations in respect of the angular value at which the collimator slit is seen from the various points of the reflecting surface.

A further embodiment of the apparatus according to the invention is provided with a second, adjustable collimator which is arranged in the beam path between the sample and the detector. This step is important notably for situations in which the angle between the beam incident on the sample and the beam emanating from the sample has a small value. In such cases it may readily occur that the cross-section of the beam incident on the sample becomes larger than the sample. The amount of radiation energy emanating from the sample then becomes dependent on the angle of incidence and the shape of the sample; for intensity measurements this leads to a situation that can be corrected only with great difficulty. Correction cannot be suitably performed either by means of the data processing computer programs used in such apparatus. It is known per se to arrange a beam limiting element in the incident beam in order to correct this problem in analytic X-ray apparatus, but the space required for this purpose is not available in many cases. It can be ensured that the detector always "perceives" a defined part of the sample by arranging the collimator in the outgoing beam and by adapting the passage width thereof to the angle of incidence, so that a correction factor thus known is obtained for the data processing computer programs.

BRIEF DESCRIPTION OF THE DRAWING

The invention will be described in detail hereinafter with reference to the Figures; therein, corresponding elements are denoted by corresponding reference numerals. In the Figures.

DETAILED DESCRIPTION OF THE PRIMARY EMBODIMENT

Figure 1:
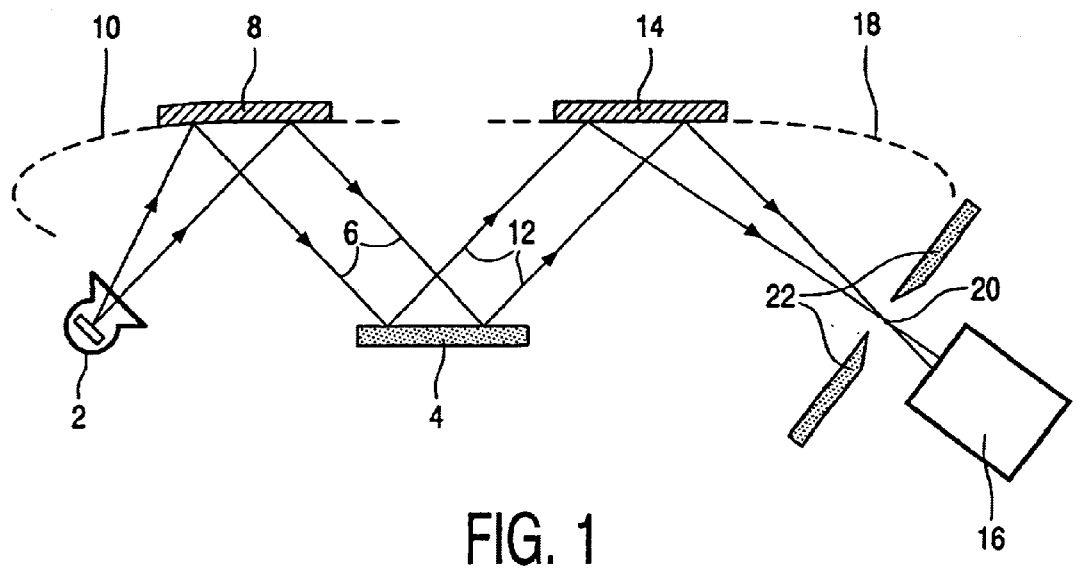
FIG. 1 shows diagrammatically a known arrangement for X-ray analysis with two parabolic multilayer mirrors.

FIG. 1 shows diagrammatically a known arrangement for X-ray analysis with two parabolic multilayer mirrors. This arrangement is notably suitable for X-ray diffraction. The arrangement includes an X-ray source 2 for irradiating a sample 4 to be analyzed by means of the arrangement. In order to parallel as well as possible the radiation 6 incident on the sample, a device for paralleling the radiation beam is arranged in the beam pat between the X-ray source and the sample, said device being a multilayer mirror 8 for X-ray reflection in the present example. The reflecting surface of this multilayer mirror has a parabolic shape as symbolically represented by a dashed line 10. The reflecting layers provided on the surface of the multilayer mirror may have a thickness which is dependent on the location, so that a so-called graded multilayer mirror is obtained. The grading is such that when the mirror is irradiated by a (from a two-dimensional point of view) point-shaped source (being a line-shaped source perpendicular to the plane of drawing when viewed three-dimensionally), the Bragg reflection condition is satisfied in each point of the multilayer mirror, with the result that a large reflecting surface is obtained for the multilayer mirror.

After diffraction of the X-rays on the sample 4, a mainly mutually parallel beam of X-rays 12 emanates from the sample. Due to interaction of the X-rays with the sample or the vicinity thereof, however, directions other than the predominant parallel direction may also occur in the beam emanating from the sample. The X-rays having such deviating directions usually affect the accuracy of the measurement; therefore, it will be attempted to eliminate such deviating beam directions from the beam 12. To this end, a further multilayer mirror 14 for X-ray reflection is arranged in the beam path between the sample 4 and an X-ray detector 16. Like the multilayer mirror 8, the multilayer mirror 14 is constructed as a graded multilayer mirror whose surface has a parabolic shape as symbolically denoted by the dashed line 18.

Due to the parabolic shape of the multilayer mirrors 8 and 14, the X-ray beam emanating from the X-ray source 2 is converted, before reaching the sample 4, into a substantially parallel beam and after the sample into a focused beam again that has a focus point in the focus 20 of the multilayer mirror 14. The collimator slit 22 is arranged at the area of said focus.

Figure 2:
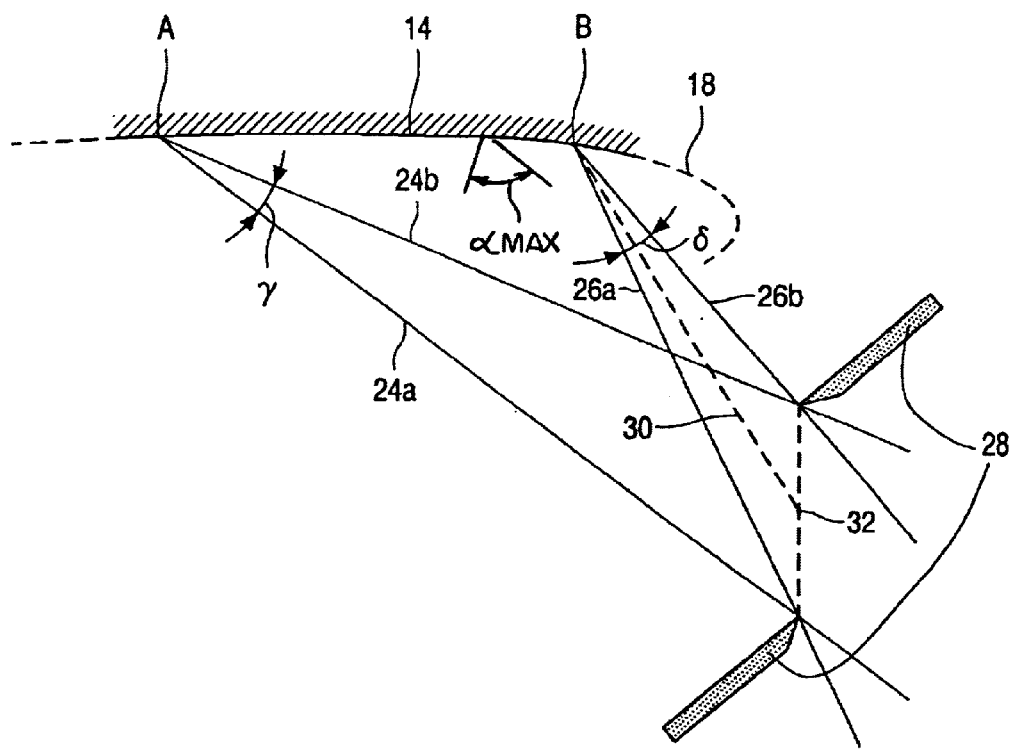
FIG. 2 shows diagrammatically a detail of an arrangement for X-ray analysis in accordance with the invention.

FIG. 2 shows diagrammatically a detail of an arrangement for X-ray analysis in accordance with the invention. A number of auxiliary lines 24a, 24b, 26a and 26b in this Figure indicate how substantially the same angular value is observed for the passage width of the collimator from every reflecting point of the multilayer mirror. (For the sake of clarity it is to be noted that said auxiliary lines do not represent rays of the X-ray beam emanating from the multilayer mirror 14, but denote only the boundaries of the angle at which the angular value of the passage width of the collimator slit 28 is seen from the points A and B, respectively.) In the embodiment shown in FIG. 2 the collimator is shaped as a collimator slit that is formed by two knife edges which are situated at different distances from the reflecting points of the multilayer mirror. The distance between the relevant reflecting point (for example, the point B) and the center 32 of the passage width of the collimator 28 can be taken as said distance, for example, as represented by the length of the line segment 30. A situation in which the angular value γ or δ of the passage width is substantially constant for the points of the surface of the multilayer mirror 14 that participate in the reflection can be achieved by a suitable choice of said difference in distances. (For the sake of clarity this reflecting part of the surface in FIG. 2 is shown to be much larger than the value corresponding to a practical situation.)

The desired effect of enhanced resolution is achieved only if the angular value (γ or δ) of the passage width of the first collimator, viewed from the reflecting points of the multilayer mirror, is smaller than the maximum angular range of the reflection $\alpha_{max}$. Because the value of the maximum angular range is of the order of magnitude of 0.05° for practical multilayer mirrors, it will be evident that the angles γ and δ are significantly exaggerated in FIG. 2.

The knife edges of the collimator are displaceable, in a manner not shown in the Figure, relative to one another in a direction transversely of the direction of the beam path through the collimator. The passage width of the collimator, and hence the resolution of the apparatus, is thus controlled without introducing deviations in respect of the angular value at which the collimator slit is viewed from the various points of the reflecting surface.

Figure 3:
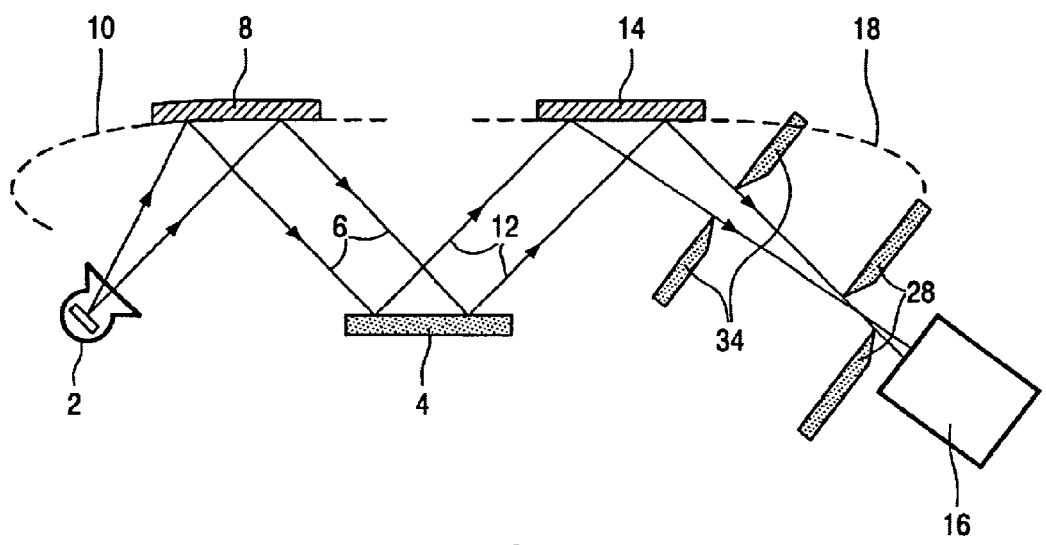
FIG. 3 shows diagrammatically a further embodiment of the invention.

FIG. 3 shows diagrammatically a further embodiment of the invention. Like in FIG. 2, the collimator 28 in this Figure is shaped as a collimator slit that is formed by two knife edges which are situated at different distances from the reflecting points of the multilayer mirror, so that the same angular value of the passage width is observed from every reflecting point of the multilayer mirror. The apparatus shown in FIG. 3 is also provided with a second collimator 34 which is arranged in the beam path between the sample 4 and the X-ray detector 16. The second collimator 34 is adjustable (in a manner not shown in the Figure) in that the knife edges are displaceable relative to one another in the direction of the beam path through the collimator. The detector will always perceive a defined part of the sample when the passage width is adapted to the angle of incidence of the radiation on the sample.

What is claimed is:

1. An apparatus for X-ray analysis of a sample, including:
    an X-ray source for irradiating the sample by means of X-rays,
    an X-ray detector for detecting X-rays emanating from the sample,
    a parabolic multilayer mirror which is arranged in a beam path between the sample and the detector and has an associated reflection angle range $\alpha_{max}$, and
    a first collimator is arranged in such a manner that it exhibits substantially the same angular value of a passage width from every reflecting point of the multilayer mirror, and
    that said angular value, viewed from every reflecting point of the multilayer mirror, is smaller than a maximum reflection angle range $\alpha_{max}$.

2. An apparatus as claimed in claim 1, wherein the angular value for the passage width of the first collimator that is observed from the reflecting mirror surface is adjustable.

3. An apparatus as claimed in claim 1, wherein the first collimator is formed by two mutually parallel knife edges which are situated at different distances from the reflecting points of the multilayer mirror.

4. An apparatus as claimed in claim 3, wherein the knife edges are displaceable relative to one another by displacement transversely of the direction of the beam path through the collimator.

5. An apparatus as claimed in claim 1, provided with a second, adjustable collimator which is arranged in the beam path between the sample and the detector.

* * * * *